(12) United States Patent
Morris

(10) Patent No.: US 8,744,163 B2
(45) Date of Patent: Jun. 3, 2014

(54) SYSTEM AND METHOD FOR LASER DISSECTION

(75) Inventor: Scott Morris, Phoenix, AZ (US)

(73) Assignee: International Genomics Consortium, Phoenix, AZ (US)

( * ) Notice: Subject to any disclaimer, the term of this patent is extended or adjusted under 35 U.S.C. 154(b) by 515 days.

(21) Appl. No.: 13/023,416

(22) Filed: Feb. 8, 2011

(65) Prior Publication Data

US 2011/0194749 A1   Aug. 11, 2011

Related U.S. Application Data

(60) Provisional application No. 61/302,816, filed on Feb. 9, 2010, provisional application No. 61/414,783, filed on Nov. 17, 2010.

(51) Int. Cl.
*G06K 9/00* (2006.01)
*C12M 1/00* (2006.01)
*G01N 1/30* (2006.01)
*C12N 1/08* (2006.01)

(52) U.S. Cl.
USPC ...... 382/133; 435/40.52; 435/270; 435/283.1

(58) Field of Classification Search
USPC .............................. 382/131; 435/40.52, 283.1
See application file for complete search history.

(56) References Cited

U.S. PATENT DOCUMENTS

| 6,040,139 | A * | 3/2000 | Bova ............................ 435/6.16 |
| 6,100,051 | A | 8/2000 | Goldstein et al. |
| 6,783,734 | B1 * | 8/2004 | Goldstein et al. ............. 422/536 |
| 2004/0085443 | A1 | 5/2004 | Kallioniemi et al. |
| 2006/0010508 | A1 | 1/2006 | Tilly et al. |
| 2006/0051736 | A1 | 3/2006 | Shields et al. |
| 2006/0199169 | A1 | 9/2006 | Lam et al. |
| 2009/0190820 | A1 * | 7/2009 | DeLa Torre Bueno ....... 382/133 |
| 2009/0247416 | A1 | 10/2009 | Can et al. |
| 2010/0099092 | A1 * | 4/2010 | Song et al. ........................ 435/6 |
| 2010/0189712 | A1 * | 7/2010 | L'Heureux et al. ......... 424/130.1 |
| 2011/0287951 | A1 * | 11/2011 | Emmert-Buck et al. .......... 506/7 |

OTHER PUBLICATIONS

Montgomery, K., et al. "Non-fiducial, shape-based registration of biological tissue," Proceedings—SPIE The International Society for Optical Engineering, 1996, pp. 224-233, Issue 2655.
International Search Report and Written Opinion for PCT/US2011/024090, dated Jun. 15, 2011.

* cited by examiner

*Primary Examiner* — Amara Abdi
(74) *Attorney, Agent, or Firm* — Knobbe, Martens, Olson & Bear LLP

(57) ABSTRACT

Systems, devices, and methods for removing areas of tissue are described. A programmable laser may remove precise areas of tissue while the tissue remains substantially frozen. The laser is programmed in part by analyzing a reference image of a representative tissue section. A software program may receive digital images of test slices. Areas of interest in the image may be selected by a user. The software program can then create and send cut instructions to the programmable laser. The laser may be configured to make perforated cuts to remove the area of interest without melting the removed section.

17 Claims, 10 Drawing Sheets

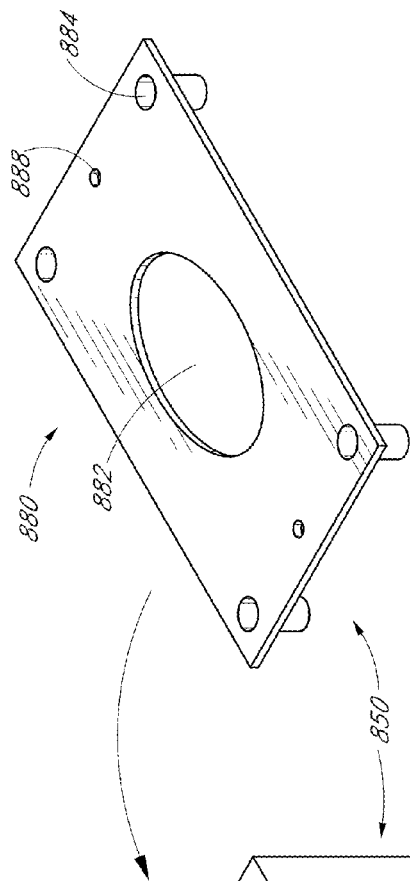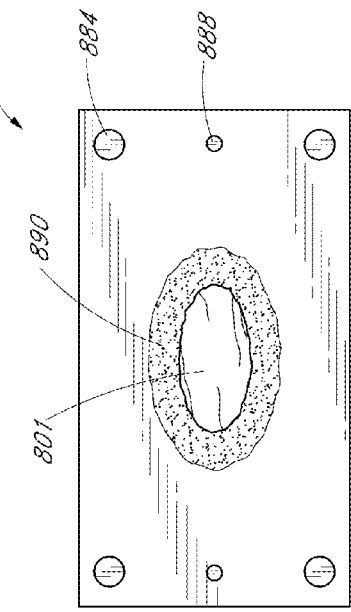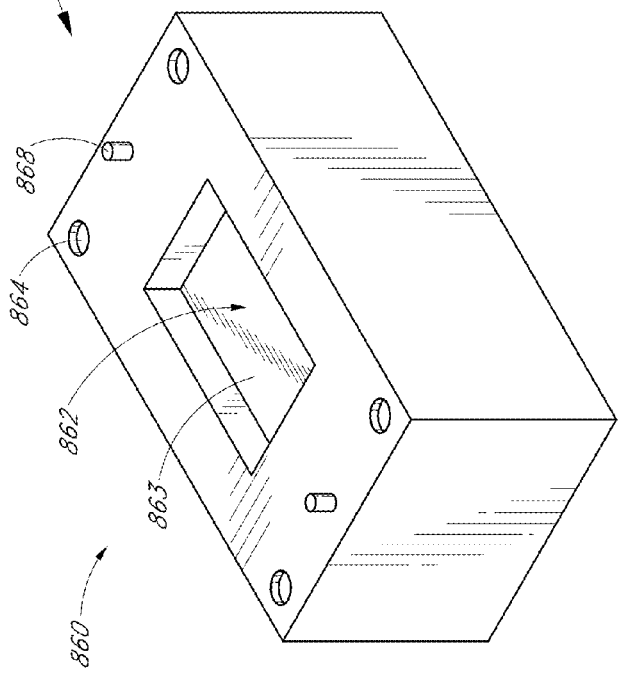
FIG. 8B
FIG. 8C

SYSTEM AND METHOD FOR LASER DISSECTION

CROSS-REFERENCE TO RELATED APPLICATIONS

This application claims priority to U.S. Provisional Application No. 61/302,816, filed Feb. 9, 2010, entitled "FLEXIBLE LASER MACRODISSECTION" and also claims priority to U.S. Provisional Application No. 61/414,783, filed Nov. 17, 2010, entitled "SYSTEM AND METHOD OF ANALYZING TISSUE." The entire content of each application referenced above is hereby expressly incorporated by reference.

BACKGROUND

1. Field

Embodiments disclosed herein relate generally to systems, devices, and methods for dissecting and analyzing tissues. More particularly, embodiments relate to high throughput imaging and laser dissection of frozen tissue samples.

2. Description of the Related Art

Diseases, such as cancer, are often identified by examining or analyzing tissue biopsies. Such tissue biopsies can contain multiple cell types that need to be identified in order to determine the proper treatment for the patient. Tissue dissection is a method to assist in isolating and removing specific cell populations from tissue samples. Normally, a tissue biopsy is removed from a patient and thin tissue slices are removed and analyzed under a microscope. In some cases, a tissue slice is stained, or treated with specific binding agents such as antibodies, to help a technician identify regions of the biopsy that are cancerous or atypical. In some cases, the tissue is digested in order to analyze expression of cellular components, such as nucleic acids or proteins.

Unfortunately, many of the experiments or stains used to identify the proper portion of a biopsy for further analysis may also materially change the biopsy tissue. For example, a technician may need to stain a sample in order to identify a cancerous region. However, the stain itself may degrade the proteins and nucleic acids in that region. Thus, the technician cannot easily identify or enrich for a cancerous population in a tissue biopsy prior to carrying out analysis of DNA, RNA, or other molecules.

The Cancer Genome Atlas ("TCGA") is a project to catalogue cancer genomes. The TCGA requires tissue samples with a high percentage of tumor nuclei and low levels of cellular necrosis to be used for genetic analysis. Accordingly, it is desirable to isolate tumor-containing regions of tissue from undesirable regions prior to molecular extraction. It is possible to physically separate desirable regions of tissue. Tissue areas may be manually removed by a technician. However, this process may be inaccurate and high resolution removal may not be possible.

Another technique to physically separate desirable regions of tissue is laser capture microdissection ("LCM"). Using this technique, a technician may look through a microscope at a stained tissue sample mounted on a slide. A transfer film may be placed over the sample. Upon identifying a cellular region of interest the technician may active a laser. The laser may cause localized heating of the transfer film, thereby activating the film. The active film can have adhesive properties causing targeted cells or cellular regions to stick to the film above. These cells can then be removed and further analyzed. However, this process often requires the tissue to be at room temperature and for the tissue sample to be fixed, stained, and/or dehydrated. Accordingly, DNA, RNA, and other molecules may be degraded using LCM.

SUMMARY

The systems, devices, and methods disclosed herein each have several aspects, no single one of which is solely responsible for their desirable attributes. Without limiting the scope of the claims, some prominent features will now be discussed briefly. Numerous other embodiments are also contemplated, including embodiments that have fewer, additional, and/or different components, steps, features, objects, benefits, and advantages. The components, aspects, and steps may also be arranged and ordered differently. After considering this discussion, and particularly after reading the section entitled "Detailed Description," one will understand how the features of the devices and methods disclosed herein provide advantages over other known devices and methods.

In one embodiment, a tissue dissection method may include obtaining at least one test slice from a tissue sample, imaging the test slice to obtain a test slice image, capturing data that identifies a target area of interest in the test slice image, and using the captured data to removing the target area of interest from the tissue sample. In one aspect, the tissue sample may be substantially frozen. In some aspects, the test slice may be stained prior to imaging the test slice. The obtaining of at least one test slice may comprise obtaining a top slice and a bottom slice from the tissue sample. The target area of interest may be removed with a programmable cutting device. In some aspects, the target area of interest may be removed with a laser. The laser may comprise an infrared laser with a wavelength between about 9 μm and 12 μm. Some aspects may further comprise cutting alignment marks in the tissue sample prior to imaging the test slice.

In some embodiments, a tissue dissection receptacle may comprise a housing having a tissue receiving area, a diffraction surface disposed at the bottom of the tissue receiving area, and a tissue holder disposed above the tissue receiving area and comprising an opening configured to retain a tissue sample. In some aspects, a diffraction surface may be configured to dissipate heat. The tissue holder may further comprise at least one restraining element. The restraining element may further comprise a magnet. The tissue receptacle may be configured to dissipate heat.

In one embodiment, a system for enriching for a population of cells of interest in a tissue sample may comprise a laser configured to cut alignment marks in the tissue sample, a digital imager configured to image a slice of the tissue sample having alignment marks, a tissue analysis module configured to receive data indicating a region of cells of interest from the slice image, and a laser configured to read the data and cut the region of cells of interest from the tissue sample in order to enrich a population of cells of interest in the tissue sample. In some aspects, the tissue analysis module may be a browser based software module. The laser may be configured to cut an "L" shaped alignment mark in the tissue sample. The laser may be configured to cut the region of cells of interest from the tissue sample by cutting a perforated cut along a border of the region of cells of interest. In some aspects, a digital imager may be configured to store an image of a slice in a server connected to a tissue analysis module. The tissue analysis module may be configured to read mouse movements to receive the data indicating a region of cells of interest. The data may be configured for the laser prior to the laser reading the data and cutting the regions of interest. In some aspects, the tissue analysis module may automatically identify regions of interest by image analysis of the tissue slice.

BRIEF DESCRIPTION OF THE DRAWINGS

The foregoing and other features of the present disclosure will become more fully apparent from the following description and appended claims, taken in conjunction with the accompanying drawings. The drawings disclose illustrative embodiments. They do not set forth all embodiments. Other embodiments may be used in addition or instead. Understanding that these drawings depict only several embodiments in accordance with the disclosure and are not to be considered limiting of its scope; the disclosure will be described with additional specificity and detail through use of the accompanying drawings.

FIG. 8B is an exploded perspective view of a tissue mount having a base and lid according to one embodiment.

FIG. 8C is a top view of a tissue mount according to one embodiment

DETAILED DESCRIPTION

Figure 1:
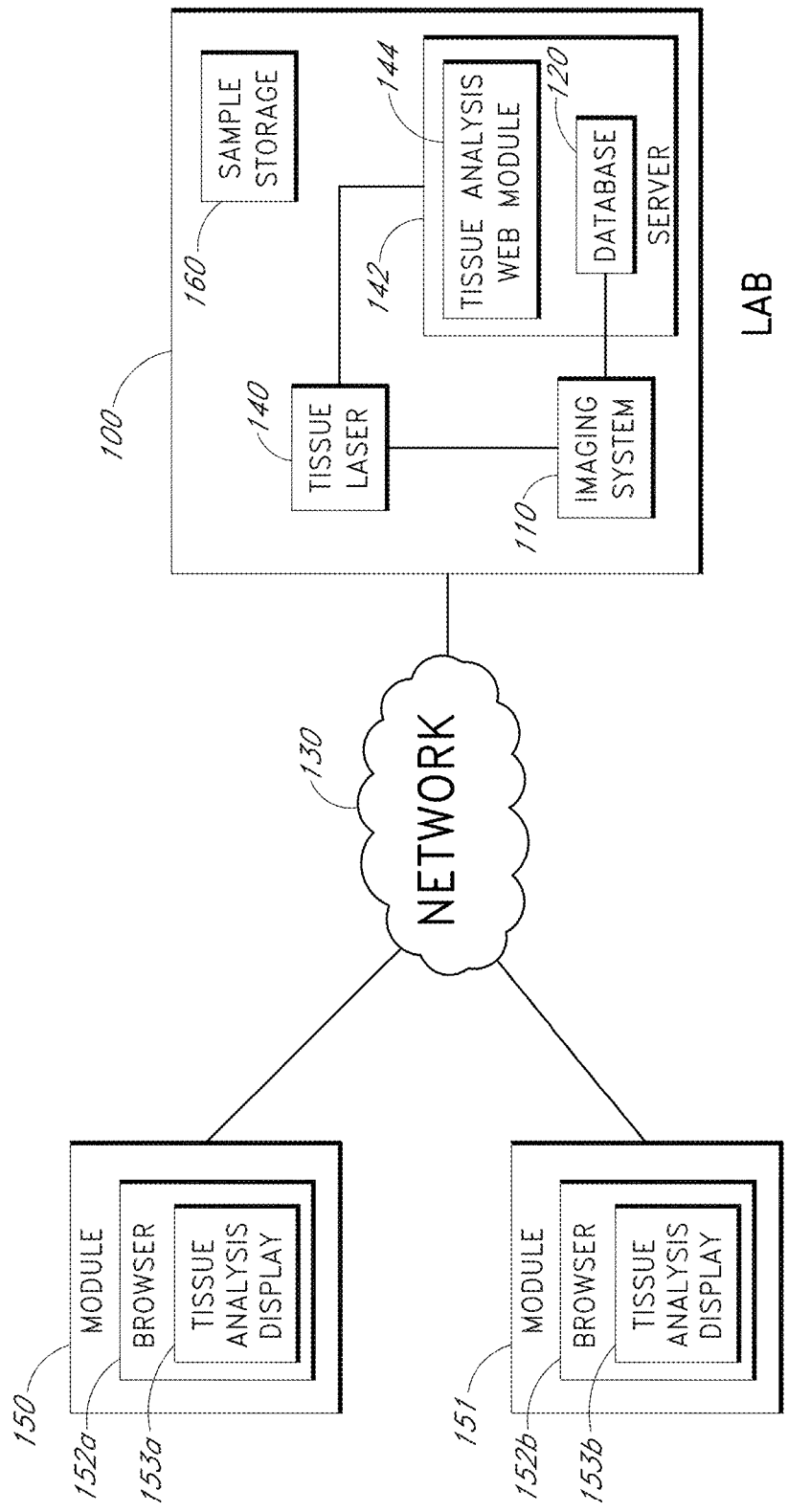
FIG. 1 is a block diagram illustrating one embodiment of a system for tissue dissection.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, and designed in a wide variety of different configurations, all of which are explicitly contemplated and make part of this disclosure.

One embodiment is a system that allows a frozen tissue biopsy to be marked with laser-generated alignment markings so that the original position of the tissue slice can be later matched with the remaining biopsy sample. In this embodiment, a frozen tissue biopsy is placed into a tissue holder, and a laser cuts a plurality of alignment holes in the sample. A slice of the frozen tissue is then taken, and the remaining biopsy can be returned to the freezer for storage. Because the tissue slice and the remaining biopsy have alignment marks, any analysis of the tissue slice can be later matched to the remaining biopsy, as will be explained more completely below.

In one embodiment, once the marked tissue slice has been removed, the slice is treated in order to visually reveal any areas of interest. For example, a tumor specific stain, or fluorescent tumor-specific monoclonal antibody may be contacted with the tissue slice in order to visually contrast any tumor portion of the slice with the non-tumor portion. In one embodiment, a high resolution image of the treated slice is then taken using a tissue imaging apparatus.

Once the tissue image is captured, the image can be displayed on a computer screen and viewed by a user, such as a physician or pathologist. The user can use on-screen tools to highlight or identify regions of interest. The areas of interest can be selected, for example, by a trained user according to the stains, cellular structures, and cell characteristics. For example, the user may use a computer mouse or trackpad to draw a line around the area, or areas, of the image corresponding to areas of the biopsy that are believed to be cancerous. Interface modules running on a computer or server can provide the on-screen drawing tools and receive the data indicative of the user selected areas. Interface modules can capture the relative position of the tissue slice image and the line drawn by the user.

Once the user has finished highlighting an area of interest in the image, the data relating to the area of interest highlighted by the user can be stored. That data can then be used to remove enriched sections from the remaining frozen tissue biopsy. In one embodiment, the remaining frozen tissue biopsy is then placed in a tissue holder within a laser dissection system. The data from the user is loaded into the laser dissection system, along with the alignment data that allows the tissue slice image, which was analyzed by the user, to be aligned with the frozen tissue biopsy. The laser dissection system, using the alignment information and input data from the user, can then precisely cut the regions of interest from the frozen tissue biopsy. This process enriches the biopsy for the precise regions of interest. The biopsy tissue can remain frozen and untreated prior to and after the enrichment procedure.

In one embodiment, the user is provided with tissue slice images using a computer that is connected through the Internet. The software running on the user's computer or server may be browser based, and thereby may be available on a wide range of computers, tablets, and other electronic devices.

Particular implementations of the subject matter described in this disclosure can be implemented to realize one or more of the following potential advantages. In some embodiments, dissected regions of tissue are not chemically treated and/or remain substantially frozen throughout the removal process. Accordingly, the quality and quantity of recovered nucleic acids may be improved. The use of one test slice of tissue (i.e. a microscope slide) as a reference to cut another piece of frozen tissue that is not directly viewed may also allow for efficient use of pathologist time. The subject matter disclosed herein may provide a high-throughput device that can robotically dissect up to multiple frozen tumor specimens simultaneously, thus improving efficiency. The subject matter disclosed may also lead to an increase in the number of qualified cases for TCGA and allow for collection of cases that were previously not considered for TCGA.

FIG. 1 illustrates a system for tissue dissection according to one embodiment. Laboratory 100 includes an imaging system 110 coupled to a server 142. The server 142 may be coupled to a laser cutting apparatus 140. Within the server 142 is a database 120 for storing tissue slice data and a tissue analysis web module 144 configured to be displayed in interface modules 150 and 151. The laboratory 100 may also include a sample storage unit 160. The laboratory 100 is connected to a network 130 which can be accessed by the interface modules 150, 151. As shown, the interface modules 150, 151 include browsers 152a-b and tissue analysis display modules 153a-b which were downloaded for display by the tissue analysis web module 144.

In one embodiment, the tissue analysis web module 144 is written in PHP with Adobe Flash® technology used to display tissue images. Additional information on the PHP language can be found on the Internet at php.net. In other embodiments, the tissue analysis display module is written in Java® for efficient download and operation in the browsers 152a-b on a user's computer.

In one embodiment, the imaging system 110 is configured to capture high resolution digital images of tissue slices. Images may be captured with various technologies and at various resolutions. Such imaging systems include ScanScope digital scanners available from Aperio Technologies Inc., in Vista, Calif., or any other system well known in the art. The imaging system 110 can create digital images of glass slides mounted with tissue samples as discussed below. The images may be in color and at a high enough resolution to visualize single cells or cell populations. In one embodiment, the imaging system 110 includes a display for viewing the image, a memory for temporarily or permanently storing the image, a processor, and an operating system for controlling the imager. The imaging system 110 may be connected to the network 130 to allow for users to access and manipulate images. In one embodiment, the network 130 is part of the Internet.

In one embodiment, the database 120 is coupled to the imaging system 110 and configured to store data representing digital images. The data base 120 may receive and store digital image data from the imaging system 110 and send digital image data over the network 130 to the interface modules 150 and 151. As shown, the database 120 is coupled to the laser cutting apparatus 140 so that data stored in the database 120 can be used to control the laser cutting apparatus 140. The database 120 may store data representing laser cut formations such as Cartesian coordinate data or CNC instructions. The database 120 may receive cut instructions over the network 130, store cut instructions, and send cut instructions to the laser cutting apparatus 140.

In one embodiment, the laser cutting apparatus 140 is configured to cut tissue. The laser cutting apparatus 140 can be programmable and can receive cutting instructions from the database 120 and/or network 130. The laser cutting apparatus 140 may include a laser mounted to mechanical components configured to move the laser longitudinally and laterally above a cutting surface. In one embodiment, the movement is CNC-controlled. The laser cutting apparatus 140 can be programmed to move to specific positions and to activate the laser at specific positions. Such positions may be referred to herein as "cut positions."

In one embodiment, the sample storage unit 160 is a freezer configured to preserve tissue samples. The freezer may be for example, a −10° C., −20° C., −80° C., or any other suitable freezer. In one embodiment, the sample storage unit 160 is a liquid nitrogen storage unit.

In one implementation, the system depicted in FIG. 1 may function as follows. A tissue sample may be provided to the laboratory 100. The tissue sample may be substantially frozen. A test slice of the tissue sample may be removed. The tissue sample can be stored in the sample storage unit 160. The test slice may be stained to aid in identifying structures on the cellular level. The test slice can be visualized and imaged with the imaging system 110. The image may be saved in the data base 120. The image may be uploaded to a network 130 and analyzed by users with interface modules 150 and 151, for example, network-based software programs. An area of interest can be identified in the image and information corresponding to the area of interest may be sent to the data base 120. Such information can be processed to result in cut instructions which may be sent to the laser cutting apparatus 140. The tissue sample can be removed from the sample storage unit 160 and placed in the laser cutting apparatus 140. The area of interest can then be removed by the laser cutting apparatus 140 programmed with the cut instructions.

Figure 2:
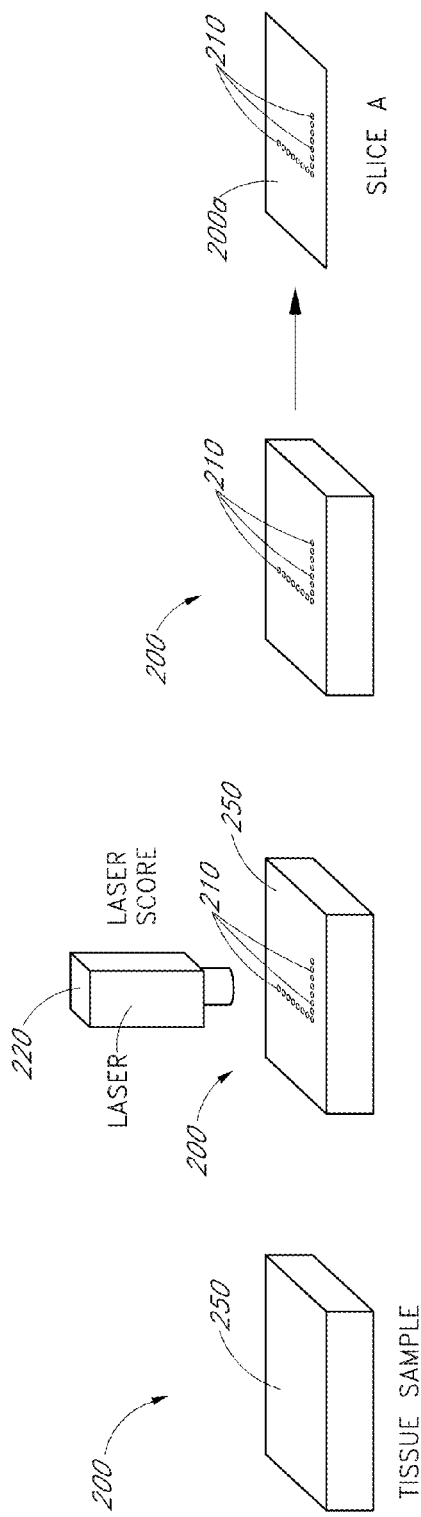
FIG. 2 is a block diagram that illustrates an embodiment of a process for scoring a tissue sample to provide an alignment reference.

FIG. 2 illustrates a process for scoring a tissue sample to provide a reference axis. The reference axis can be used to correlate the relative positioning of areas in the tissue sample. The reference axis can be used to align images with imaging analysis software. For example, a reference point or reference axis can be used to establish a coordinate system. Image analysis software can calculate the relative distances from the reference axis. This information can be transformed into cut instructions for a programmable laser cutting apparatus.

In the embodiment illustrated in FIG. 2, the process begins by providing a tissue sample 200. The tissue sample 200 may be substantially frozen. In some embodiments, the tissue sample 200 remains below about −10° C. The process continues by placing the tissue sample 200 in the laser cutting apparatus. The laser cutting apparatus may be programmed to move to a plurality of cut positions. The laser 220 may be configured to penetrate less than the total thickness of the tissue sample under the cut positions.

In one embodiment, the laser 220 is configured to cut tissue without damaging nucleic acids. In one embodiment, the laser 220 emits a wavelength in the infrared spectrum, for example a wavelength in the range of about 9-12 μm. In one embodiment, the laser 220 is a carbon dioxide ($CO_2$) laser that emits wavelength of about 10.6 μm. The power and speed settings of the laser 220 may be adjustable and programmable. A suitable laser cutting apparatus 140 may be the VLS6.60 with a 60 watt $CO_2$ Free-Space Gas Slab Laser and a 2" focus lens available from Universal Laser Systems in Scottsdale, Ariz. The laser can be configured to cut frozen tissue by rapidly vaporizing water in the frozen tissue. Other suitable devices and methods that do not implement a laser may also be used to cut tissue. For example, a CNC machine with an attached router or knife blade may be used as a substitute.

In one embodiment, alignment marks 210 are made in the tissue sample 200 along two approximately perpendicular lines. As illustrated, alignment marks are made on a top surface 250 of the tissue sample 200. However, alignment marks may be made on any surface and/or multiple surfaces. The process continues by removing the tissue sample 200 from the laser cutting apparatus.

The process continues by removing a test slice 200a from tissue sample 200. The test slice 200a may be cut and removed with a cryostat-microtome device or with any suitable device or method well known in the art. The remainder of the tissue sample 200 can be stored in the sample storage while the test slice 200a is further processed and imaged. Although FIG. 2, depicts one test slice 200a removed from a top surface 250 of the tissue sample 200, a plurality of test slices may be removed from any surface of the tissue sample 200. For example, any combination of a top section, bottom section, and/or a side section may be removed. The test slices may also be removed at any angle relative to the top or side surface or from any depth. As will be described in detail later, in one embodiment, test slices are cut from both the top and bottom of the sample 200, and the cutting area is determined using both test slices. In one embodiment, test slices are cut from the top and the side to better understand the three dimensional structure of the tissue sample 200.

As shown in FIG. 2, the test slice 200a includes alignment marks 210 that are in an "L" shaped configuration. The alignment marks 210 can function as an alignment reference because they are visible in images of the test slice 200a and the sample 200. The axis of the slices and sample can be aligned with the alignment marks 210 to provide a known reference from which the cut instructions for the laser can be determined.

Figure 3:
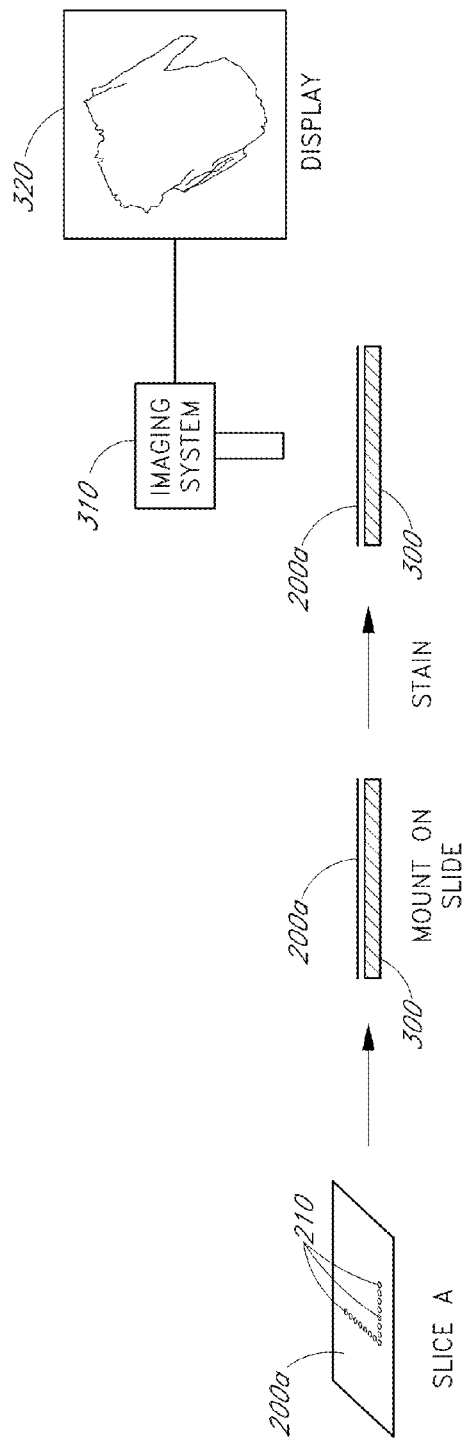
FIG. 3 is a block diagram that illustrates an embodiment of a process for staining and imaging test slices of a tissue sample.

FIG. 3 illustrates a process for staining and imaging a test slice 200a of the tissue sample 200. The test slice 200a is mounted on a slide 300. The test slice 200a may be stained with any stain well known in the art to enhance the contrast or highlight structures of interest. In one embodiment, the test slice 200a is stained with hematoxylin and eosin (H&E) stain. Other identification techniques such as, for example, special staining, immunohistochemistry staining, fluorescence in situ hybridization, Förster resonance energy transfer ("FRET"), or chromogenic in situ hybridization, may also be used to determine areas of interest. The process continues by imaging the stained slide with an imaging system 310 to obtain an image on a display 320 of the tissue slice 200a. The imaging system may be based on a variety of microscopic methods, including bright field, dark field, phase contrast, fluorescence, confocal laser scanning, and electron microscopy. The imaging system may be the ScanScope XT from Aperio. The image may be analyzed using software such as ImageScope or Webscope from Aperio. The image can be stored, and later disseminated to users such as pathologists.

Figure 4:
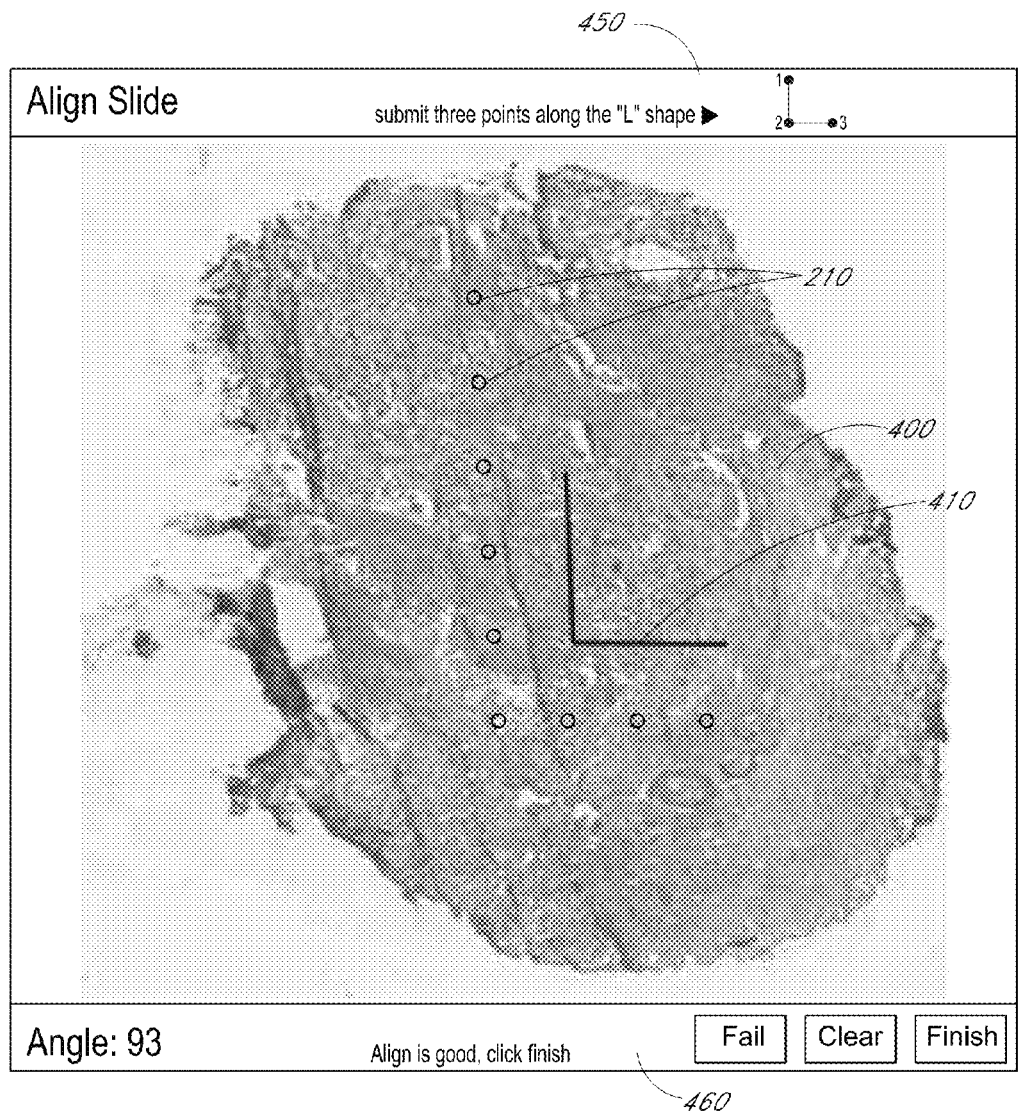
FIG. 4 is a screen shot of a tissue section image displayed in a software environment.

FIG. 4 illustrates a screen shot of a test slice image manipulated in a software environment of one embodiment of the invention. In the illustrated embodiment, the tissue analysis display module 153 is accessed by downloading data from the tissue analysis module 144 running on the server 142 in the lab 100. As shown, the test slice image 400 includes alignment marks 210. Instructions running in the browser 152a allow rotation of the image to align the "L" shaped alignment marks 210 with an origin axis 410. The origin axis 410 can provide a reference point for the laser cutting instructions. The tissue analysis display module 153a can prompt the user with an alignment prompt 450. In the illustrated embodiment, the alignment prompt 450 cues a user to select three points to form an origin. For example, a user can select three points over three alignment marks to establish an origin by moving a mouse over the selected points and clicking. The analysis display module can provide feedback to the user in a feedback prompt 460. For example, the software can verify that the three points form two lines that intersect at about 90°. The user can clear the selected access or select finish if the alignment is satisfactory.

Figure 5B:
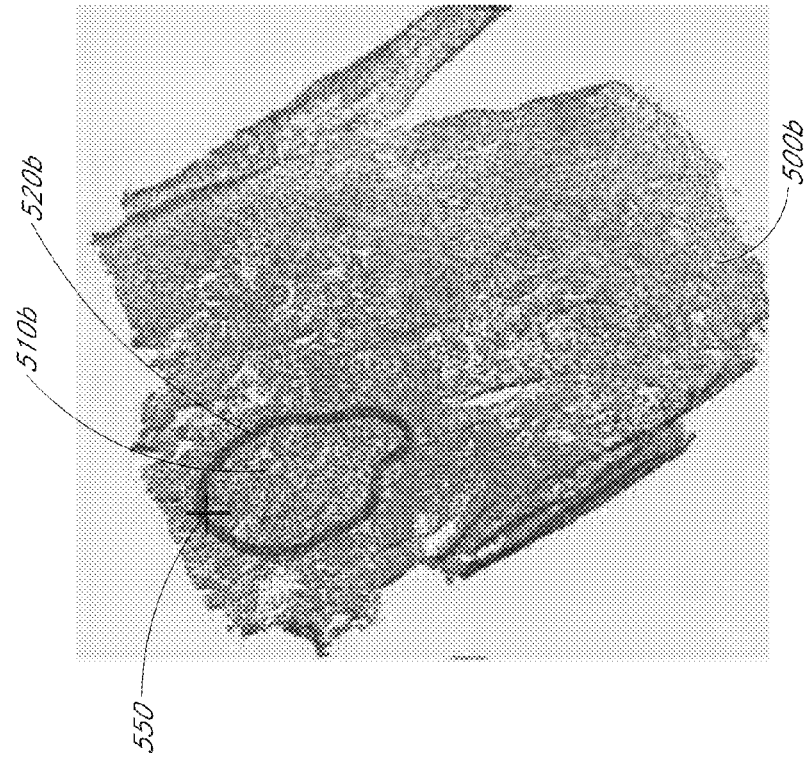
FIGS. 5A-5B are screen shots that illustrate tissue section images that have been highlighted with user defined areas of interest.
Figure 5A:
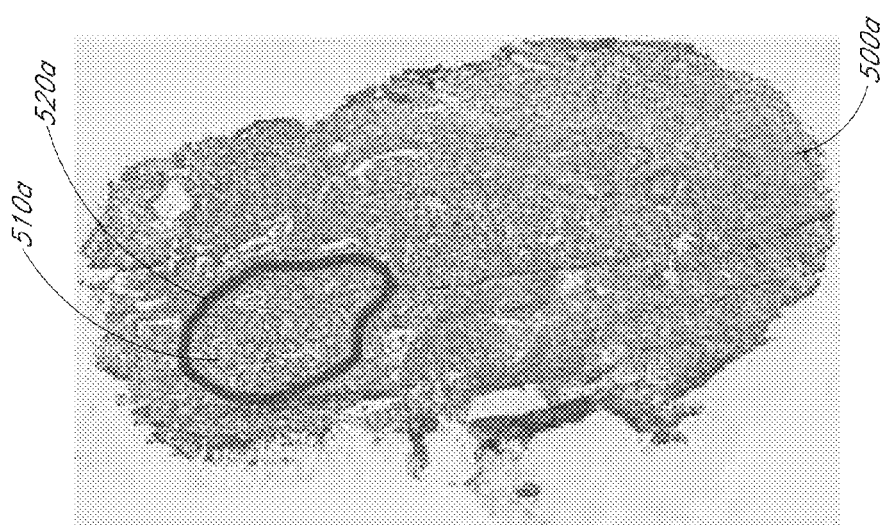

FIGS. 5A-5B illustrate images of test slice images 500a-b with user defined areas of interest 510a and 510b. Image analysis software allows a user to use a mouse or trackpad to select areas of interest 510a and 510b in test slices 500a and 500b with, for example, a cursor 550. The areas of interest 510a and 510b may be identified by forming lines 520a and 520b around the respective selected areas, thus circumscribing the area of interest. The areas of interest 510a and 510b may have been discovered to have a high percentage of cancer cells in one embodiment. The areas of interest may not include areas of necrosis in one embodiment. The areas of interest may not include stromal cells in one embodiment. It should be realized that using this system, a pathologist can use their computer to encircle and define any pre-chosen area of interest depending on the patient and tissue sample that was used for analysis. For example, lung tissue samples from patients suspected for having lung cancer would be analyzed for cancerous tissue.

Areas of interest may also be identified in images by image analysis software. Such software may employ cellular recognition algorithms that can recognize areas of interest based on cellular sizes, shapes, colors, densities and/or other characteristics. In one embodiment, the software recommends an area of interest to a user. The user may then accept the recommended area or modify the area of interest. In one embodiment, the software may be trained to identify areas of interest. For example, the software can store image information for areas of interest selected by users. This stored image information can then be used by the software to compare to new images and make recommendations based on comparisons to previously selected areas of interest. In one embodiment, the software is fully automated. For example, the software can analyze the image, select an area of interest, formulate cut instructions, and send the cut instructions to the cutting apparatus.

Figure 6:
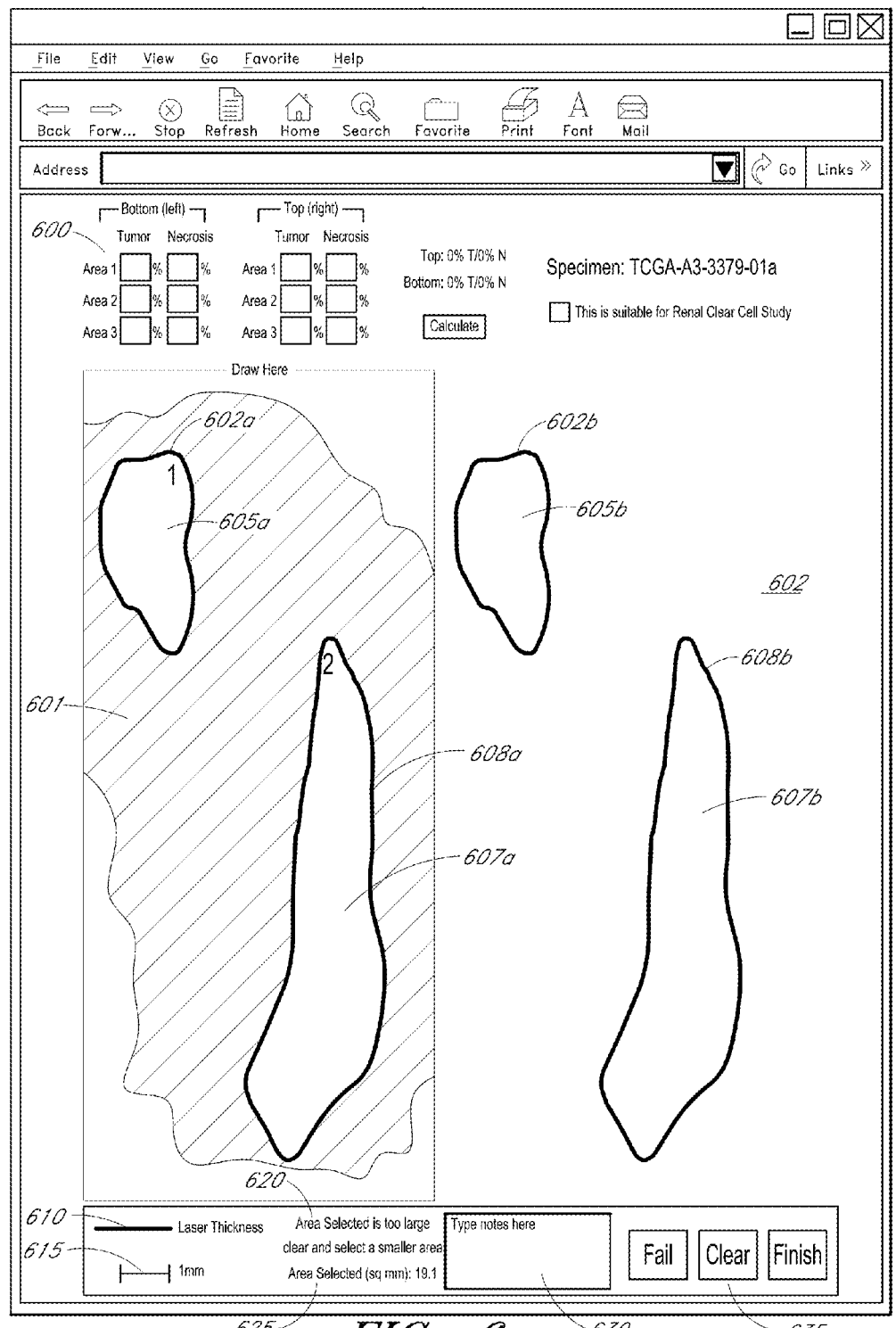
FIG. 6 is a screen shot of an image analysis software program according to one embodiment.

FIG. 6 illustrates a screen shot of an image analysis software program according to one embodiment. The screenshot includes selection window 601 and viewing window 602. The viewing window 602 displays the test slice image. The selection window 601 is used to select areas of interest in the image of the test slice. For example, a user can select areas of interest 605a and 607a in the selection window 601 by clicking and dragging a mouse cursor to form lines 602a and 608a that surround the area. Corresponding areas may appear in the viewing window 602 as lines 602b and 608b and areas of interest 605b and 607b. The software program may alert the user, for example by alert 620, if the selected area is unable to be cut by the cutting apparatus. An area may not be able to be cut, for example, if the selected area is too small, or too large, or too complex a shape for the cutting apparatus to cut. The size of the selected area may also be calculated by the program and displayed by area display 625.

With continued reference to FIG. 6, an annotation area 630 may be provided for notes and/or for data results to be entered. A scale 615 may be provided to display the relative size of the test slice. A laser thickness display 610 may also provide the relative thickness of the laser cut lines. A user input 635 may clear or finalize the selected areas. In the illustrated embodiment, the software program is run on a browser such as Microsoft Internet Explorer® or Apple Safari®. A user data input 600 for a variety of study-related data elements may be provided. The data displayed or entered into user data input 600 may contain components automatically calculated based on other entries in the form and/or the shapes of the regions selected.

Figure 7A:
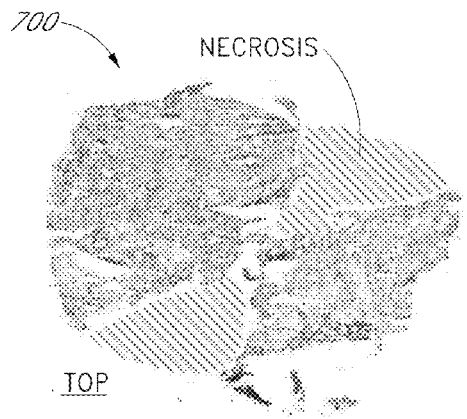
FIGS. 7A-7E are screen shots of tissue sections and illustrate one embodiment of a process for determining an area to be removed from a tissue sample.
Figure 7B:
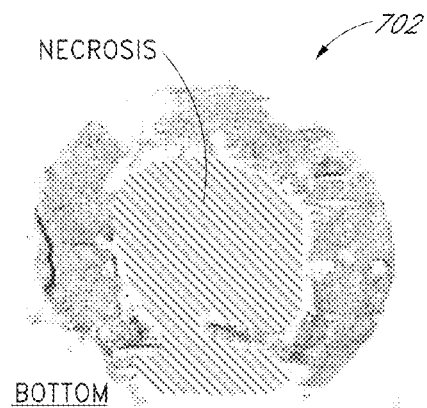
Figure 7C:
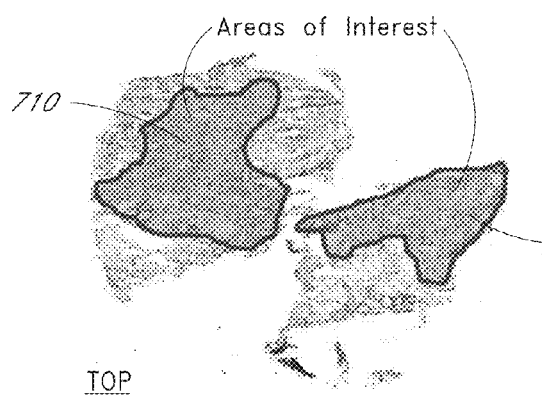
Figure 7D:
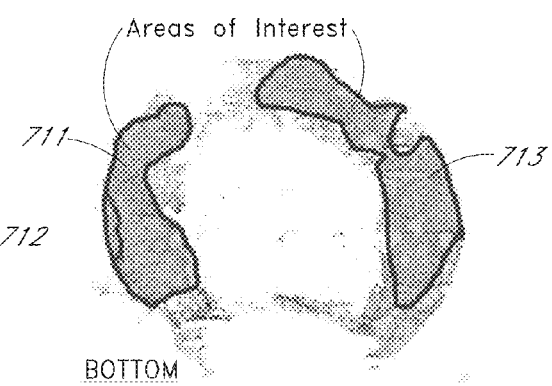
Figure 7E:
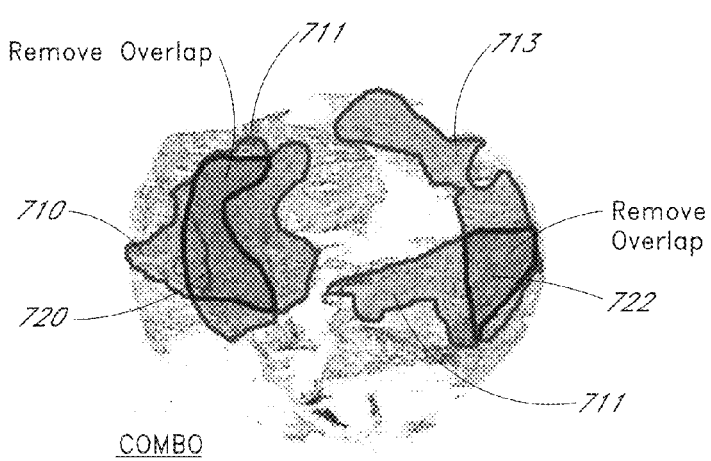

FIGS. 7A-7E illustrate a process for determining one or more areas to be removed from a tissue sample according to one embodiment. FIG. 7A illustrates a test slice removed from the top side 700 of a tissue sample while FIG. 7B illustrates a test slice removed from the bottom side 702 of the same tissue sample. The test slices shown are stained and imaged. FIG. 7C illustrates user selected areas of interest in the test slice removed from the top side 710 and 712 of the tissue sample while FIG. 7D illustrates user selected areas of interest in the test slice removed from the bottom side of the tissue sample 711 and 713. Areas of necrosis may be visualized and avoided. The top and bottom images may then be combined as shown in FIG. 7E. Image analysis software may determine the overlapping user selected areas of interest 720 and 722. These overlapping areas of interest 720 and 722 may then be used to create cut instructions. The cut instructions can be sent to the cutting apparatus and only the overlapping areas can be removed from the tissue sample. Accordingly, a homogonous cell population may be more likely to be removed.

Figure 8A:
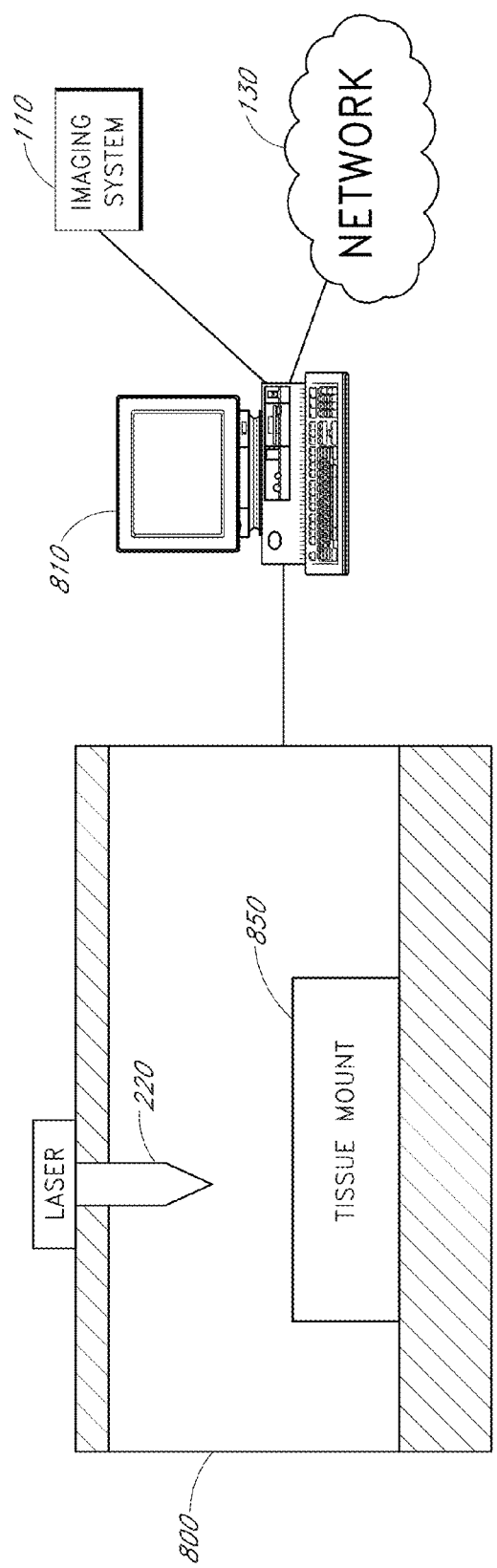
FIG. 8A is a block diagram that illustrates one embodiment of a computer controlled tissue laser cutting system.

FIG. 8A illustrates a schematic view of a laser cutting system according to one embodiment. The laser cutting system includes a laser cutting apparatus 800 coupled to a controller 810, such as a personal computer. The controller 810 may also be coupled to a network 130 and a digital imaging system 110. The laser cutting apparatus 800 may include a laser 220 and a sample mount 850. The laser 220 can move in at least two directions over the sample mount 850 below. The laser movement and cutting properties can be programmed and/or controlled by controller 810.

FIG. 8B illustrates a perspective view of a tissue holder or mount according to one embodiment. In the illustrated embodiment, the sample mount 850 comprises a tissue receptacle 860 and a tissue holder 880. The tissue holder 880 may include an opening 882 to receive a tissue sample. The tissue sample may be frozen. The tissue sample may be secured within the opening 882 with a tissue cement such as Tissue-Tek O.C.T. or any other suitable compound well known in the art. A portion of the tissue sample may protrude above and/or below the opening 882. A protruding portion may be sliced and removed with a cryostat-microtome device. The tissue holder 880 may be stored in a freezer.

The tissue holder 880 may include at least one restraining element 884 configured to secure the tissue holder 880 to the tissue receptacle 860. The restraining element 884 may comprise a magnet. The tissue holder 880 may also include a locating element 888 such as a post or a hole configured to align the tissue holder 880 with the tissue receptacle 860. In one embodiment, the locating element 888 comprises hole configured to be received by a post on the tissue receptacle. The tissue holder 880 may be configured to dissipate heat. The tissue holder 880 may be formed with any suitable metal. In one embodiment, the tissue holder 880 is made of aluminum.

In one embodiment, the tissue receptacle 860 includes a receiving area 862. The receiving area 862 may be located below the opening 882 in the tissue holder 880 when the tissue holder 880 is secured to the tissue receptacle 860. The receiving area 862 may include a surface 863 configured to diffract light. For example, the surface 863 may be scored, or include grooves, or be coated with light absorbing material. The tissue receptacle 860 may include at least one restraining element 864 and/or locating element 868 to align the tissue holder and/or secure the tissue holder 880 in position over the receiving area 862. The tissue receptacle 860 may be configured to dissipate heat. For example, the tissue receptacle 860 may be substantially hollow and/or surrounded by a cooling system. In one embodiment, the interior and sides of the tissue receptacle 860 are contacted with dry ice. The tissue receptacle 860 may be formed with any suitable metal. In one embodiment, the tissue receptacle 860 is made of aluminum.

FIG. 8C illustrates a top view of a tissue mount according to one embodiment. A tissue sample 801 can be mounted within the opening in the tissue holder 880 and secured within the opening with tissue cement 890. The tissue holder 880 may be placed over the tissue receptacle 860 in the same orientation in which the alignment marks were previously made. Multiple sample mounts may be provided in a laser cutting apparatus such that multiple tissue samples may be cut at one time.

Figure 9:
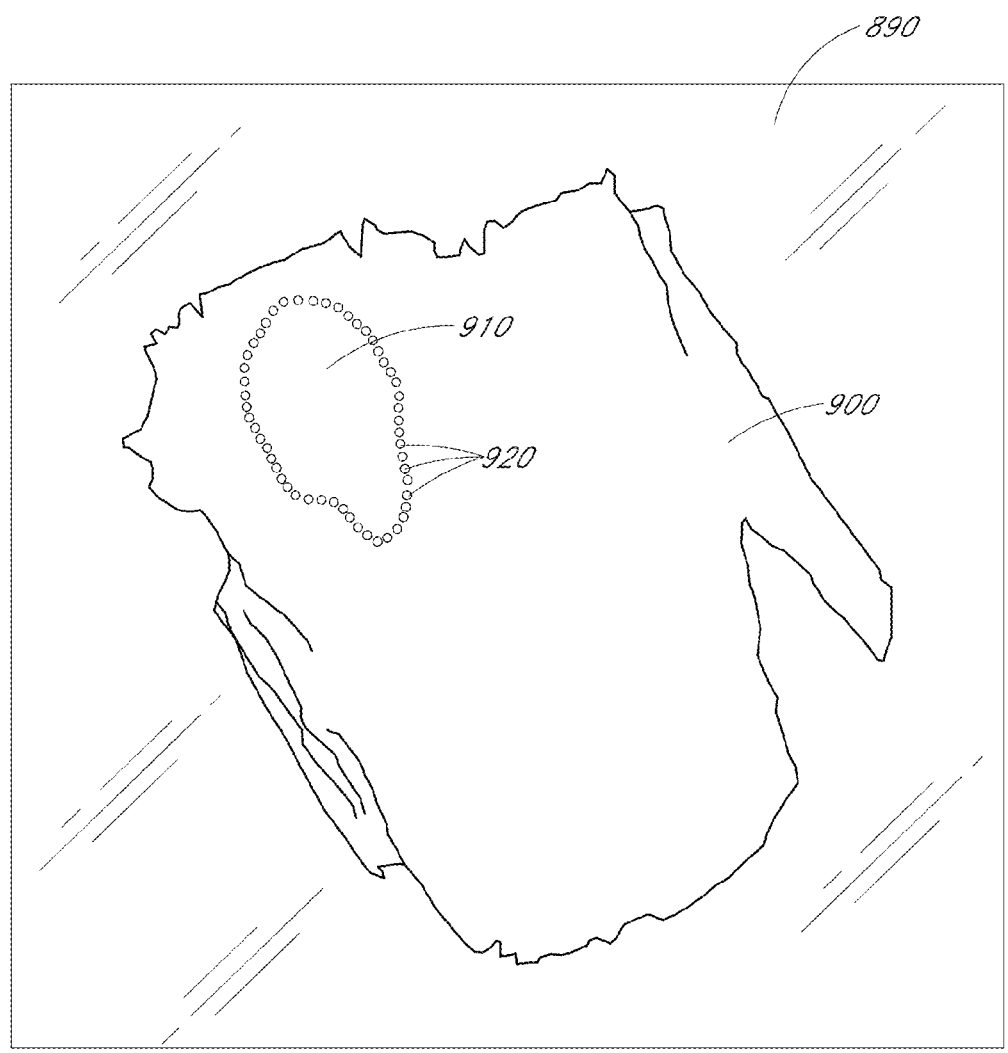
FIG. 9 is a top view of a tissue sample after partial cutting by a laser cutting apparatus.

FIG. 9 illustrates a top view of a tissue sample after partial cutting by a laser cutting apparatus. A tissue sample 900 can be secured within the opening of a tissue holder with tissue cement 890. As shown, the laser cutting apparatus can be configured to make perforations 920 along the border of an area of interest 910. For example, the laser can pass over the tissue sample 900 and the laser can be activated to cut separate perforations 920 at positions that form a line surrounding, or circumscribing, the area of interest 910. The laser formed perforations 920 can be made, for example, about every 100, 200, 300, or 500 microns along the line surrounding the area of interest 910. In addition, the laser can be configured to penetrate less than the total depth of the tissue sample 900 such that the laser is activated multiple times over each perforation to cut through the total depth of the tissue sample 900. The laser can make multiple passes over the tissue sample 900 and the laser can be activated at the same cut positions. In some implementations, the laser may make 20-200 passes over the tissue sample 900, for example about 60 passes. By making a plurality of cuts at each perforation 920 in the tissue 900, the system may allow the tissue sample 900 and area of interest 910 to remain substantially frozen. In contrast, in some embodiments when the laser is used to cut completely through the tissue sample 200 in a single pass, the tissue may begin to melt due to the high temperature of the laser as it cuts each perforation. After cutting, the area of interest 910 may fall or be tapped into the tissue receptacle below. The spacing of each perforation may be adjusted to accommodate how much pressure it takes to remove an area of interest from the remaining tissue sample after laser cutting.

Figure 10A:
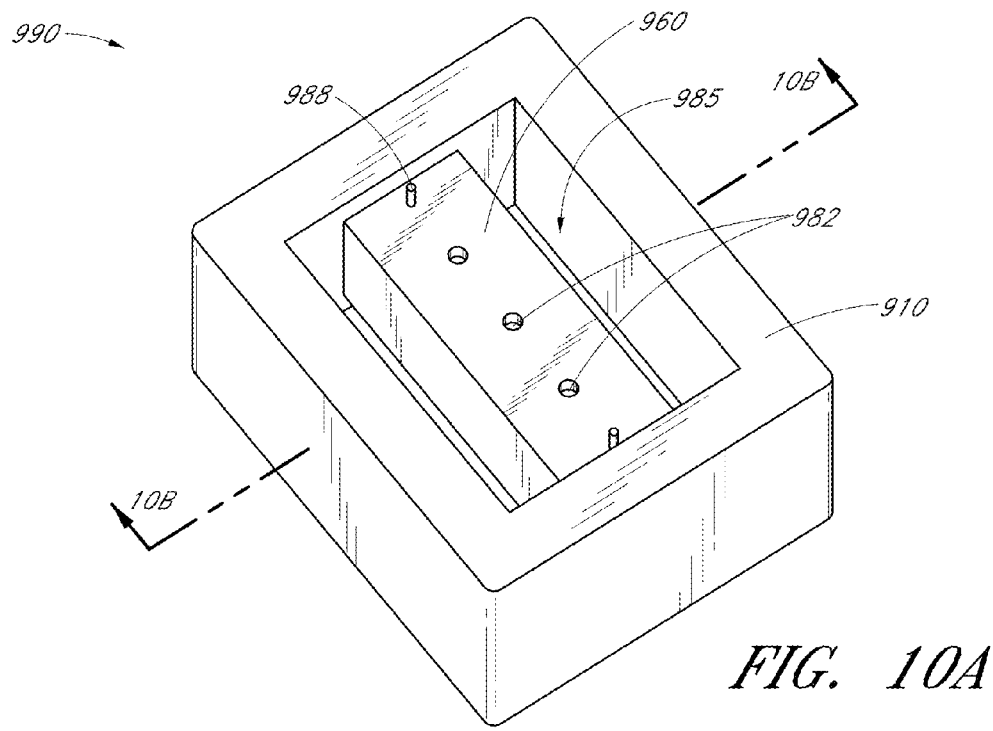
FIG. 10A is a perspective view of an alternate embodiment tissue mount.

FIG. 10A illustrates a perspective view of a tissue mount according to another embodiment. In the illustrated embodiment, the tissue mount 990 includes an insulating shell 910 surrounding a tissue receptacle 960. A cavity 985 is formed between the tissue receptacle 960 and insulating shell 910 and may be filled with dry ice and/or isopropyl alcohol to maintain a tissue sample in a substantially frozen state. A fan (not shown) may be provided to circulate cold air over the tissue mount 990. The tissue receptacle 960 can include a locating element 988 for aligning and securing a tissue holder to the tissue receptacle 960. One example of a tissue holder 880 can be found in FIG. 8B. The tissue receptacle 960 includes openings 982 which can lead to a tissue receiving area.

Figure 10B:
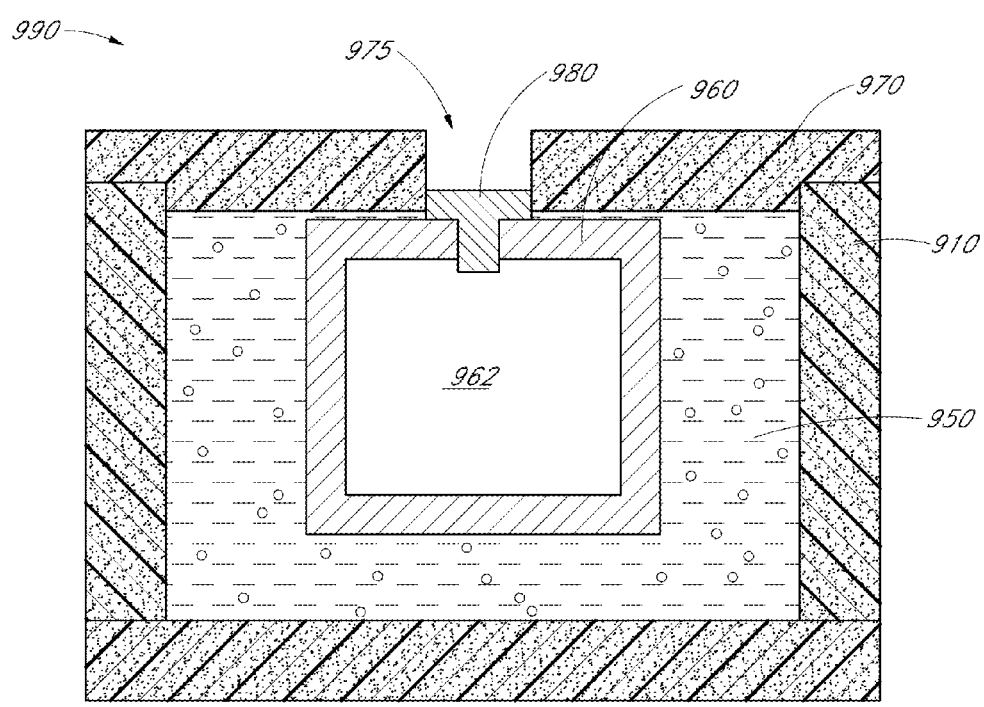
FIG. 10B is a side view of the tissue mount illustrated in FIG. 10A along the line 10B-10B.

FIG. 10B illustrates a cross-sectional side view of the tissue mount 990 illustrated in FIG. 10A along the line 10B-10B. The cavity 985 in between the tissue receptacle 960 and insulating shell 910 is shown as filled with a cooling liquid 950. A tissue holder 980 can be located and secured over the tissue receptacle 960. An insulating cover 970 can be provided over the insulating shell 910 to further insulate the tissue receptacle 960. The insulating cover 970 can have an opening 975 through which a laser may pass through and cut tissue samples held in the tissue holder 980. The cut tissue sections can fall into the tissue receiving area 962 and be kept substantially frozen until retrieved.

Using the System

The system for tissue dissection may be used as follows in one embodiment of the invention. A technician starts with a block of frozen tissue. The tissue block is mounted to a tissue holder 880 with O.C.T. while on dry ice. The tissue holder is then secured to a tissue receptacle 860 and placed within the laser cutting apparatus. The tissue receptacle is placed on dry ice to keep the tissue block frozen. Magnets are used to secure the tissue holder to the tissue receptacle. The tissue holder is keyed or configured such that it can only be mounted to the tissue receptacle in one unique orientation to ensure that the tissue block can be re-aligned with the system easily. The laser cutting apparatus is then programmed to cut alignment marks in the tissue block. The alignment marks are in the shape of an "L" so that a later slice of the tissue can be realigned with its remaining tissue block.

The tissue holder is then removed from the laser cutting apparatus and a slice of tissue is removed from the top surface of the tissue sample while the tissue sample remains in the tissue holder. The test slice is removed with a cryostat-microtome and the remaining tissue block, still cemented into the holder, is stored in a −80° C. freezer. The test slice is then stained and mounted to a slide. The slide is then placed into a digital slide imaging system and a high resolution image of the stained tissue slice is captured into the system.

The image is imported into the tissue analysis software program and thereafter manipulated to be more reviewable on screen. A technician brings up the tissue slice image on screen and the alignment marks are visualized. An origin of the image can be made relative to the alignment marks that are clearly shown in the tissue slice image. The image can then be either analyzed or stored for later transmission to a pathologist. A pathologist can then accesses the tissue image in the tissue analysis display module that is programmed to run in a web browser of the pathologist's computer. The tissue analysis display module allows the pathologist to select areas of interest in the image based on the visualized stain. The areas are selected by the pathologist left clicking a computer mouse and dragging a line around the area of interest. Once the pathologist has identified that area of interest in the tissue analysis display module, the data corresponding to the coordinates of the line surrounding the area of interest are stored on a server accessible by the technician.

The technician loads the frozen remaining tissue sample back into the laser system and uses the data generated by the pathologist to cut a pattern of perforations around the area of interest. The laser cut instructions from the pathologist or the technician can further include a laser power setting and number of passes the laser makes over the sample depending on the thickness of the frozen tissue sample.

The area of interest can then be mechanically removed by pressing the area, or areas, of interest until they break free as plugs taken from the frozen tissue sample. The area of interest is then further analyzed by the technician as it has been enriched for the cell types desired by the pathologist. For example, the tissue area of interest may be analyzed using any kit suitable for frozen specimen well known in the art. Molecules of the tissue, including DNA, RNA, proteins, lipids, carbohydrates, and metabolites, may be collected and analyzed using, for example, Southern Blots, Northern Blots, Western Blots, DNA/RNA/protein sequencing analysis, DNA/RNA/protein microarray, functional protein assays, enzyme-linked immunosorbent assays ("ELISA"), and/or PCR tests to identify features of the cells within the area of interest.

Although this method has been described by processing frozen tissues, the lack of pretreatment requirements and a flexible cutting environment make it suitable for any type of tissue, whether frozen or at room temperature. For example, a freshly resected piece of tissue could be cut at 37° C. and high humidity, using an adjacently cut frozen section as a template. In this scenario, pure populations of living cells could be collected for cell culture.

In addition to cutting, other methods can be employed with the devices disclosed herein. For example, the laser or some other device could be used to kill cells without removing them or to introduce a marker that can be detected later.

Example 1

Tissues were prescreened, and those containing greater than 70% tumor nuclei were submitted to TCGA. Twelve cases of kidney renal cell carcinoma and lung adenocarcinoma that failed the full BCR pathology process were dissected using the laser cutting method and device described above. Ten previously disqualified cases became qualified for molecular extraction.

No impact was observed in the time or labor involved in histology, and a decrease in the effort required for pathology review was observed. The additional time required for the dissection step was minimal (about 15-20 minutes per study). In general, the laser cutting method and device was able to nearly eliminate necrosis, and was able to eliminate enough normal nuclei to qualify the cases. This is attributable to the tendency of necrosis to occur in large regions and the diffuse distribution of normal nuclei (especially endothelial cells).

Microscopic evaluation revealed that cutting was consistently completed within 50 µm of target. Visible damage to tissues in the cutting area was minimal (damage extended about 10-15 µm from the cut line).

Example 2

Renal cell carcinoma portions were dissected using the laser cutting method and device described above. RNA was extracted and analyzed from the removed areas of interest. The results were compared to a cohort of renal cell carcinoma cases collected under the same protocol and extracted under TCGA protocols. RNA and DNA were extracted via the current TCGA SOP (Allprep+mirVana). Quality of RNA was assessed via the RNA integrity number (RIN) as assessed by the Bioanalyzer (Agilent). Both sets of tissue have RIN's drawn from the same distribution, and no significant difference in RIN was observed via a Welch's T-Test ($p>0.05$). Accordingly, the laser cutting method and device described above may enrich frozen specimens for tumor nuclei without causing RNA degradation that is measurable by the Agilent Bioanalyzer.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description and claims may refer to elements or features as being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically. Thus, although the various schematics shown in the figures depict example arrangements of elements and components, additional intervening elements, devices, features, or components may be present in an actual embodiment (assuming that the functionality of the depicted circuits is not adversely affected).

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that any of the various illustrative logical blocks, modules, cores, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, cores, and circuits described in connection with the aspects disclosed herein may be implemented within or performed by an integrated circuit (IC), an access terminal, or an access point. The IC may comprise a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. The logical blocks, modules, cores, and circuits may include antennas and/or transceivers to communicate with various components within the network or within the device. A general purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The functionality of the modules or cores may be implemented in some other manner as taught herein. Furthermore, the functionality described herein (e.g., with regard to one or more of the accompanying figures) may correspond in some aspects to similarly designated "means for" functionality in the appended claims.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

The functions described may be implemented in hardware, software, firmware, or any combination thereof. If implemented in software, the functions may be stored on or transmitted over as one or more instructions or code on a tangible, non-transitory computer-readable medium. Computer-readable media includes both computer storage media and communication media including any medium that facilitates transfer of a computer program from one place to another. A storage media may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. A computer-readable medium may be in the form of a non-transitory or transitory computer-readable medium. Also, any connection may be properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. In summary, it should be appreciated that a computer-readable medium may be implemented in any suitable computer-program product.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A tissue dissection method comprising:
   providing a substantially frozen tissue block;
   cutting alignment marks into the tissue block;
   obtaining at least one test slice from the tissue block, wherein the test slice and the tissue block have alignment marks, and wherein the alignment marks define an alignment reference that allows the test slice to be aligned in its original orientation with respect to the tissue block;
   imaging the test slice to obtain a test slice image;
   capturing data that identifies a target area of interest in the test slice image; and
   using the captured data to remove the target area of interest from the tissue block.

2. The method of claim 1, wherein the test slice is stained prior to imaging the test slice.

3. The method of claim 1, wherein obtaining at least one test slice comprises obtaining a top slice and a bottom slice from the tissue block.

4. The method of claim 1, wherein the target area of interest is removed with a programmable cutting device.

5. The method of claim 4, wherein the target area of interest is removed with a laser.

6. The method of claim 5, wherein the laser comprises an infrared laser with a wavelength between about 9 µm and 12 µm.

7. A system for enriching for a population of cells of interest in a substantially frozen tissue block, comprising:
   a laser configured to cut alignment marks in the tissue block, such that when a test slice is removed from the tissue block, the test slice and the tissue block have alignment marks, and wherein the alignment marks define an alignment reference that allows the test slice to be aligned in its original orientation with respect to the tissue block;
   a digital imager configured to image a slice of the tissue block having the alignment marks;
   a tissue analysis module configured to receive data indicating a region of cells of interest from the slice image; and
   a laser configured to read the data and cut the region of cells of interest from the tissue block in order to enrich a population of cells of interest in the tissue block.

8. The system of claim 7, wherein the tissue analysis module is a browser based software module.

9. The system of claim 7, wherein the laser is configured to cut an "L" shaped alignment mark in the tissue sample.

10. The system of claim 7, wherein the laser is configured to cut the region of cells of interest from the tissue block by cutting a perforated cut along a border of the region of cells of interest.

11. The system of claim 7, wherein the digital imager is configured to store the image of the slice in a server connected to the tissue analysis module.

12. The system of claim 7, wherein the tissue analysis module is configured to read mouse movements to receive the data indicating a region of cells of interest.

13. The system of claim 7, wherein the data is configured for the laser prior to the laser reading the data and cutting the regions of interest.

14. The system of claim 7, wherein the tissue analysis module can automatically identify regions of interest by image analysis of the tissue slice.

15. The method of claim 1, wherein the alignment marks define an "L" shape.

16. The method of claim 1, further comprising aligning the tissue block with the alignment reference.

17. The system of claim 7, further comprising:
   an analysis display module configured to verify whether the test slice is aligned with the alignment reference.

* * * * *